United States Patent [19]
Yamaguchi

[11] Patent Number: 5,935,996
[45] Date of Patent: Aug. 10, 1999

[54] COMPOSITION FOR STIMULATING OSTEOGENESIS AND PREVENTINGREDUCTION OF BONE SALT

[75] Inventor: Masayoshi Yamaguchi, Shizuoka, Japan

[73] Assignee: Taishi Foods Company Ltd., Aomori-ken, Japan

[21] Appl. No.: 08/940,969

[22] Filed: Sep. 30, 1997

[30] Foreign Application Priority Data

Oct. 11, 1996 [JP] Japan ................................ 8-287344

[51] Int. Cl.⁶ .................................................. A61K 31/35
[52] U.S. Cl. ...................... 514/460; 514/451; 514/457
[58] Field of Search ................................ 514/451, 460, 514/470, 469

[56] References Cited

U.S. PATENT DOCUMENTS 5,506,211  4/1996  Barnes et al. ............................... 514/27

OTHER PUBLICATIONS

"Absorption and Excretion of the Soy Isoflavone Genistein in Rats", King et al, American Institute of Nutrition, 1995, pp. 176–182.

"Dietary Soybean Protein Prevents Bone Loss in an Ovariectomized Rat Model of Osteoporosis", Arjmandi et al, American Institute of Nutrition, 1995, pp. 161–167.

"Growth–Inhibitory Effects of the Natural Phyto–oestrogen Genistein in MCF–7 Human Breast Cancer Cells", Pagliacci et al, European Journal of Cancer, vol. 30A, No. 11, 1994, pp. 1675–1682.

"Genistein, a Dietary–Derived Inhibitor of In Vitro Angiogenesis", Fotis et al, Proc. National Academy of Science USA, vol. 90, Apr., 1993, pp. 2690–2694.

"Soybean Isoflavones Improve Cardiovascular Risk Factors without Affecting the Reproductive System of Peripubertal Rhesus Monkeys", Anthony et al, American Institute of Nutrition, 1995, pp. 43–50.

"Genistein Suppresses Cellular Injury Following Hepatic Ischemia/Reperfusion", Yamamoto et al, Transplantation Proceedings, vol. 28, No. 2, Apr., 1996; pp. 1111–1115.

"Differential Effects of Calcium–Regulating Hormones on Bone Metabolism in Weanling Rats Orally Administered Zinc Sulfate", Yamaguchi et al, Metabolism, vol. 35, No. 11, November, 1986, pp. 1044–1047.

"Action of Zinc on Bone Metabolism in Rats Increases in Alkaline Phosphatase Activity and DNA Content", Yamaguchi et al, Biochemical Pharmacology, vol. 35, No. 5, 1986, pp. 773–777.

"Stimulatory Effect of Zinc on Bone Formation in Tissue Culture", Yamaguchi et al, Biochemical Pharmacology, vol. 36, No. 22, 1987, pp. 4007–4012.

"Zinc Stimulation of Bone Protein Synthesis in Tissue Culture—Activation of Aminoacyl–tRNA Synthetase", Yamaguchi et al, Biochemical Pharmacology, vol. 37, No. 21, 1988, pp. 4075–4080.

"Effect of Vitamin $K_2$ (menaquinone–7) on Bone Metabolism in the Femoral–Metaphyseal Tissues of Normal and Skeletal–Unloaded Rates: Enhancement with Zinc", Ehara e al, Research In Experimental Medicine, 1996, pp. 196:171–178.

*Primary Examiner*—Theodore J. Criares
*Attorney, Agent, or Firm*—Nikaido Marmelstein Murray & Oram, LLP

[57] ABSTRACT

It is an object of this invention to provide a composition capable of being used for foods and pharmaceuticals, which stimulates osteogenesis and has an effect for preventing reduction of a bone salt content, and which is useful for therapy and prevention of osteoporosis, fracture and the like.

The composition is characterized by containing an isoflavone as a main active ingredient. The composition be preferably ingested so that the concentration of genistein in blood in one hour after ingestion is $10^{-7}$ M or more. Further preferably, the composition contains zinc salt whose concentration in blood is $10^{-7}$ M or more.

3 Claims, No Drawings

COMPOSITION FOR STIMULATING OSTEOGENESIS AND PREVENTINGREDUCTION OF BONE SALT

BACKGROUND OF THE INVENTION

1. Field of the Invention

The present invention relates to a composition for stimulating osteogenesis and preventing reduction of a bone salt content, which can be used for therapy and prevention of osteoporosis, fracture and the like.

2. Description of the Related Prior Art

The osteoporosis is tends to give rise to lumbar pressure fracture, fracture of femoral neck and the like due to the reduction of the bone salt content per unit capacity which is the mode of a disease. These fractures are the main cause for old-aged person to be confined the bed for a long time. Further, postmenopausal estrogen secretion for women may reduce so that the bone salt content rapidly decreases, and they are susceptible to osteoporosis. Additionally, it is not easy to increase the reduced bone salt content, and it is difficult to treat the osteoporosis. Accordingly, it is important to prevent the osteoporosis. To this end, it is necessary to increase the bone salt content from the youth and to suppress rapid reduction of postmenopausal bone salt content. Also even in young people, diseases causing from calcium ponerty owing to unbalanced diet are increasing.

Ingestion of sufficient calcium from a meal and moderate exercises are important for the prevention of osteoporosis and diseases causing from calcium ponerty. To this end, various sources for supplying calcium have been developed. However, it has been known that intestinal absorption of calcium may be affected by the state of calcium salt and other coexisting foodstaffs. Studies of a calcium absorbing mechanism and developments of foodstaffs for stimulating the absorption thereof or preventing the reduction of bone salt content have been demanded.

Soybeans contain many kind of isoflavones which include daidzin, genistin, glystin and those having a malonyl group bonded thereto, and aglycon thereof. Recently, it has been reported that these ingredients have an anti-tumor activity, a female hormone-like activity and the like, upon which attention has been focused.

The absorption of isoflavone was examined for rats by supplying an isoflavone to confirm the absorption thereof in blood after ingestion of the feed (R. King, J. Nutr. 126: 176–183, 1996). Further, it has been also reported that the isoflavone thus orally administerd may increase the bone density of femur (Uesugi et al., Society of Nutritious Food In Japan, 1996).

Further, it has been reported by in vivo experiment (Metabolisum, 35, 773, 1986, Biochem. Pharmacol. 35, 773, 1986) and in vitro experiment (Biochem. Pharmacol., 36, 4007, 1987, 37, 4075, 1988) that zinc plays an important part as an active factor for stimulation of osteogenesis and for mineralization. Moreover, there is shown that zinc stimulates a bone protein synthesis (Biochem. Pharmacol., 37, 4075, 1988).

SUMMARY OF THE INVENTION

It is an object of this invention to provide a composition capable of being used for foods and pharmaceuticals, which may stimulate osteogenesis and prevente the reduction of a bone salt content, and which is useful for therapy and prevention of osteoporosis, fracture and the like.

The composition for stimulating osteogenesis and for preventing the reduction of a bone-salt content according to the present invention is characterized by containing an isoflavone as a main active ingredient.

More specifically, the composition contains preferably genistin contained in isoflavone, and more preferably, genistein as a main active ingredient.

Further, it is preferable that these isoflavone, genistin, and genistein are used in combination with a zinc salt. These isoflavone, genistin, genistein and zinc are administered so that the concentration in blood after one hour of ingestion may be $10^{-7}$ M or more.

The present inventors studied intensively on a factor affecting on calcium metabolism, and they have found that genistein and zinc salt may enhance osteogenesis. The present invention has been completed on the basis of this new finding.

The function and advantageous effect of the composition according to the present invention were elucidated by experiments in which the composition of the present invention was added to a femoral metaphysical tissue (cultured cells) of an old-aged rat of 50 age in week and cultured.

That is, genistein, genistin, and zinc salt were added to a bone tissue culture, and an activity of alkaline phosphatase for accelerating mineralization, a DNA content as an index for the number of cells in the bone tissue, and calcium as a bone salt content were measured, as a result of which the following fact was clarified.

It was contemplated that the alkaline phosphatase activity, DNA content and calcium increase significantly, and the co-presence of genistein, genistin, and zinc salt enhance their respective effects due to the synergistic effect. It is expected from the aforementioned result that the composition of the present invention has activities for accelerating osteogenesis capable of preventing the reduction of the bone salt content resulting from weakened bone-metabolism caused by aging and is useful for therapy of osteoporosis and fracture and prevention of osteoporosis.

DETAILED DESCRIPTION OF THE PREFERRED EMBODIMENTS

The present invention will be explained hereinafter in greater detail referring to experimental examples.

Experimental Methods

1. Culture medium and reagent

Dulbecco's modified Eagle's medium and a penicillin-streptomycin mixed solution (5000 U/ml–5000 $\mu$ g/ml) were obtained from Gibco Laboratories (Grand Island N.Y., USA). Bouine serum albumin and cycloheximide were obtained from Sigma Chemical Co. (St. Louis, Mo., USA).

Dipicolonate, zinc sulfate and other reagents used are products of high purity, and were obtained from Wako Pure Chemical Industries Co., Ltd. Genistein and genistin were obtained from Sigma Chemical Co. Genistein and genistin were dissolved in ethanol, and other reagents were dissolved in distilled water.

2. Animal

Wistar rats (female, 4 age in week and 50 age in week) was obtained from Japan SLC (Hamamatsu Japan). The rat freely ingested laboratory chow (1.1% Ca, 1. 1% P) made by Oriental Yeast Co. and distilled water.

3. Bone tissue culture method

The rats were anesthetized with diethyl ether, and femur was taken out aseptically. Marrow was washed in an ice-cold 0.25 M sucrose solution and separated into a diaphysis and a metaphysis tissue. The metaphysis tissue of femur was cut into smoll pieces, genistein, genistin and zinc sulfate were added into Dulbecco's modified Eagle medium (containing 0.25% BSA, 1% penicillin-streptomycin) (added so that final concentration is $10^{-5}$ M), and cultured for 24 hours in a 35 mm dish. This culture was carried out in a $CO_2$ incubator under the conditions of 5% $CO_2$–95% au at 37° C.

4. Measurement of zinc and calcium contents in bone tissue

The cultured metaphysis tissue of femur was lightly washed in a 0.25 M sucrose solution and dried for 6 hours in a dryer at 100° C. After the dried weight was measured, the tissue is put into a test tube, and 3 ml of concentrated sulfuric acid was added thereto and digested at 120° C. for 24 hours. The resulting product was used as a sample solution, and the zinc content and the calcium content were measured by an atomic absorption spectrophotometry. The zinc and calcium contents were expressed by $\mu$g or mg per 1 g of bone dried weight.

5. Measurement of bone alkaline phosphatase activity

The metaphysis tissue of femur was washed with an ice-cold 0.25 M sucarose solution, and hamogenized in 3 ml of an ice-cold 6.5 mM barbital buffer (PH 7.4) and ultra-centrifuged for 60 seconds. Further, it was centrifuged for 5 minutes at 3000 rpm, and its supernatant fraction was used to measure enzyme activity. The bone alkaline phosphatase activity was measured in accordance with Walter and Schutt methods. The enzymatic reaction was started by adding 0.05 ml of the enzyme-solution to 2 ml of 0.1 M diethanolamine hydrochlide buffer (pH 9.8) containing p-nitrophenol disodium phosphate as a substrate, and incubation was carried out for 30 minutes at 37° C. The reaction was stopped by adding 10 ml of 0.5 N NaOH, and liberated p-nitrophenol was measured by a spectrophotometer (405 nm). The enzymatic activity was expressed by enzyme proteid content (mg) using p-nitrophenol content (n mol) produced by reaction through incubation for one minute.

6. Measurement of DNA content in bone tissue

The metaphysis tissue of femur was washed with an ice-cold 0.25 M sucrose solution, and after removal of water, the wet weight thereof was measured. This was homogenized in 4.0 ml of 0.1 N NaOH and shaked for 24 hours at 4° C. and extracted. Thereafter, it was centrifuged for 5 minutes at 3000 rpm, and a supernatant fraction was used as a sample for measuring DNA. DNA content was determined by the method of a Ceriotti method. One ml of concentrated hydrochrolic acid and 1.0 ml of 0.04% indole solution were added to 2.0 ml of the sample, an aluminum cap was put over a test tube, which was heated for 10 minutes in a boiling water, and the reaction was stopped by rapid cooling in ice. Extraction with 4.0 ml of chloroform for 3 to 4 minutes was repeated several times, and the DNA content was measured by a spectrophotometer (490 nm). The DNA content was expressed by a wet bone tissue (g).

7. Statistical analysis

The significant test of each measured value was carried out using Student's t-test. 5% or less at a probability level was determined to have a significant difference.

8. Results

With respect to the bone components (an activity of enzyme alkaline phosphat ase for accelerating mineralization, a DNA content as an index of the number of cells in the bone tissue, and calcium as a bone salt content in the bone tissue) in the metaphysis tissue of rat femur (cancellous bone), a remarkable reduction of the bone components was noticed in young-aged rats (4 age in week) as compared with the elderly-aged rats (50 age in week).

TABLE 1

Reduction of bone components in metaphysis tissue of elderly-aged rat

| Bone Components | Young-aged rat (4 age in week) | Old-age rat (50 age in week) |
|---|---|---|
| Zinc ($\mu$g/g dry weight) | 27.2 ± 2.59 | 11.5 ± 0.52 |
| Calcium (mg/g dry weight) | 222.6 ± 6.4 | 172.8 ± 10.3 |
| DNA (mg/g wet weight) | 3.163 ± 0.173 | 2.510 ± 0.056 |
| Activity of enzyme | | |
| Alkaline phosphatase activity ($\mu$mol/min/mg protein) | 2.315 ± 0.095 | 0.731 ± 0.067 |

The values indicate the result obtained from the bone tissue of six rats (average value±standard deviation).

TABLE 2

Effects of zinc and genistein of bone components in metaphysis tissue of femur of elderly-aged rat

| Treatment | Calcium (mg/g dry wt.) | DNA (mg/m wet wt.) | Alkaline phosphatase activity ($\mu$mol/min/mg protein) |
|---|---|---|---|
| Zinc not added | | | |
| Control | 181.0 ± 4.1 | 2.456 ± 0.052 | 0.910 ± 0.046 |
| Genistein | 214.7 ± 3.9 | 3.196 ± 0.060 | 1.572 ± 0.070 |
| Genistin | 203.6 ± 4.0 | 3.159 ± 0.038 | 1.543 ± 0.062 |
| Zine added | | | |
| Control | 217.6 ± 10.4 | 3.074 ± 0.185 | 1.520 ± 0.125 |
| Genistein | 272.0 ± 2.3 | 3.849 ± 0.064 | 2.596 ± 0.110 |
| Genistin | 202.3 ± 4.3 | 3.127 ± 0.047 | 1.833 ± 0.054 |

The values indicate the measured result after culturing the bone tissue of six rats (mean value±standard deviation).

The metaphysis tissue of femur obtained from elderly-age rat was cultured (24 hours). When genistein ($10^{-5}$ M), genistin ($10^{-6}$ M) and zinc sulfate ($10^{-5}$ M) were added in the culture medium, the amount of said all bone components were significantly increased.

It is found that when the incubation is carried out for 24 hours under the co-presence of genistein ($10^{-5}$ M) and zinc sulfate ($10^{-5}$ M), the respective effects are enhanced to bring forth the synergistic effect. In the combination of genistin ($10^{-6}$ M) and zinc sulfate ($10^{-5}$ M), the synergistic effect appears only with respect to the alkaline phosphatase activity.

It has been found from the aforementioned results that a composition comprising the combination of genistein in soybean and zinc of essential trace metal to a living body is effective for therapy for accelerating ossification and is capable of preventing reduction of the bone salt content resulting from weakness of bone metabolism caused by aging. This leads to a possibility capable of preventing osteoporosis by foodstuffs.

EXAMPLE 1 Formulation

| | |
|---|---|
| Genistein | 50 g |
| Zinc sulfate | 50 g |
| Corn starch | 125 g |
| Crystalline cellulose | 25 g |

The above components were uniformly mixed, and 200 ml of an aqueous hydroxypropyl cellulose solution were added thereto. The resulting mixture was granulated using a granulator equipped with 0.5 mm screen and immediately rounded by a rounding apparatus, after which it was dried to obtain granules.

EXAMPLE 2 'tofu'(Soybean curd)

| Soybean milk | 1000 g |
|---|---|
| Genistein | 5 g |
| Oyste eatract (1% or more as zinc) | 5 g |

The above ingredients are uniformly mixed, and a coagulant for soybean curd was added thereto to obtain 'tofu'.

As described above, the composition of the present invention having the effects of stimulating osteogenesis and preventing reduction of bone salt content can not only be taken as an easily ingestible granule, but also, can be ingested easily without a feeling of physical disorder as a daily food. Therefore, this composition is particularly useful for therapy and prevention of osteoporosis of elderly-aged person. Also for young people, this composition provides high effects for therapy and prevention of diseases resulting from a calcium caused by unbalanced diet.

What is claimed is:

1. A method for accelerating ossification and preventing reduction of bone salt content which comprises administering to a mammal in need thereof an effective amount for accelerating ossification and preventing reduction of bone salt content of a composition containing synergistic effective amounts of genistein and a zinc salt.

2. A pharmaceutical composition comprising synergistic effective amounts of genistein and a zinc salt.

3. The composition of claim 2, further comprising tofu.

* * * * *